(12) United States Patent
Koehler et al.

(10) Patent No.: US 6,500,980 B1
(45) Date of Patent: Dec. 31, 2002

(54) PROCESS FOR PREPARING AMINO DERIVATIVES OF C-H-ACID COMPOUNDS

(75) Inventors: Guenther Koehler, Marl (DE);
Wolfgang Kleemiss, Haltern (DE);
Frank Bauer, Haltern (DE)

(73) Assignee: Degussa AG, Duesseldorf (DE)

( * ) Notice: Subject to any disclaimer, the term of this patent is extended or adjusted under 35 U.S.C. 154(b) by 0 days.

(21) Appl. No.: 09/863,253

(22) Filed: May 24, 2001

(30) Foreign Application Priority Data

May 26, 2000 (DE) .......................................... 100 26 108

(51) Int. Cl.$^7$ .......................................... C07C 229/24
(52) U.S. Cl. ........................................ 560/171; 560/170
(58) Field of Search ................................ 560/170, 171; 564/258, 253, 254, 255, 256, 260, 416, 418

(56) References Cited

U.S. PATENT DOCUMENTS 5,861,533 A * 1/1999 Bauer et al. ............... 564/258

FOREIGN PATENT DOCUMENTS

| DE | 954 873 | 12/1956 |
| DE | 2 352 706 | 4/1974 |
| EP | 0 517 041 | 12/1992 |
| EP | 0 811 607 | 12/1997 |

OTHER PUBLICATIONS

Paine, J.B., Pyrrole Chemistry. An Improved Synthesis of Ethyl Pyrrole–2–Carboxylate Esters from Diethyl Aminomalonate, *J. Org. Chem.*, 1985, 50, 5598–5604.

* cited by examiner

*Primary Examiner*—Shailendra Kumar
(74) *Attorney, Agent, or Firm*—Oblon, Spivak, McClelland, Maier & Neustadt, P.C.

(57) ABSTRACT

A process for preparing amino derivatives of C—H-acid compounds of the general formula I

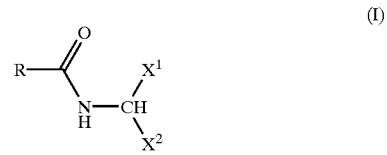

(I)

where R is an alkyl group, a cycloaliphatic radical, an aryl radical, an alkylaryl radical or an aralkyl radical, and $X^1$ and $X^2$ are identical or different electron-withdrawing groups, by reacting compounds of the general formula II

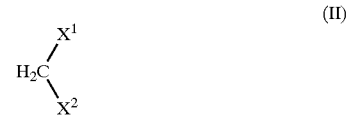

(II)

with nitrous acid, where the nitrosation is carried out in the presence of from 1 to 10 mol of a carboxylic anhydride, and the reaction product is subjected to catalytic hydrogenation, where appropriate after removing the salts derived from the reaction. Compounds of the general formula I are useful intermediates for compounds which can be used in the pharmaceutical and agricultural sectors.

20 Claims, No Drawings

PROCESS FOR PREPARING AMINO DERIVATIVES OF C-H-ACID COMPOUNDS

BACKGROUND OF THE INVENTION

1. Field of the Invention

The invention relates to a process for preparing amino derivatives of C—H acid compounds of the general formula I:

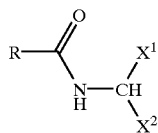

where R is an unbranched or branched alkyl group having from 1 to 10 carbon atoms, in particular a methyl, ethyl or propyl radical, a cycloaliphatic radical having from 5 to 12 carbon atoms, an aryl radical, in particular a phenyl or a naphthyl radical, an alkylaryl radical having from 7 to 12 carbon atoms, such as the ethylphenyl radical, or an aralkyl radical having from 7 to 12 carbon atoms, such as the benzyl or the phenyl ethyl radical, and $X^1$ and $X^2$ are identical or different electron-withdrawing groups, by reacting C—H-acid compounds represented by formula II:

where $X^1$ and $X^2$ are as defined above, with nitrous acid liberated from a nitrite by another acid, in the presence of from 1 to 10 mol of a carboxylic anhydride (based on the compound of the formula II), whereby practically complete conversion of the compound of the formula II is achieved, and the reaction product, the O-acyl derivative of the nitrosation product of II, is passed to a catalytic hydrogenation, optionally after removing the salts derived from the reaction.

2. Description of the Background

Amino derivatives represented by formula I are useful intermediates for compounds which can be used in the pharmaceutical and agricultural sectors. The corresponding N-acetamido malonic esters may be mentioned as examples.

There are a variety of processes known for the nitrosation of malonic acid derivatives, such as esters, amides, imidoesters and malononitrile.

For example, J.B. Paine et al. in J. Org. Chem. 50, 5598–5604 (1985), describe a process for preparing diethyl hydroxyiminomalonate, in which an aqueous solution of sodium nitrite is slowly added to a solution of diethyl malonate in glacial acetic acid, sodium hydroxide solution is added to the reaction mixture, which is a homogeneous solution, and the reaction product is removed from the aqueous phase comprising sodium acetate by extraction with diethyl ether. The process produces sodium acetate in the form of an aqueous solution in amounts which in molar terms are approximately 4 times the amount of diethyl malonate used.

In DE-A-23 52 706, ethyl cyanoacetate is first reacted with hydrogen chloride in absolute alcohol to give diethyl monoimidomalonate hydrochloride, and this is dissolved in acetic acid. An aqueous solution of sodium nitrite is then gradually added to the solution, and once the nitrosation reaction has ended, water is added to the reaction mixture. Again, the reaction product is removed from the aqueous phase which comprises the sodium acetate produced by extraction with a solvent.

EP-A-0 517 041 describes an example of the preparation of dimethyl hydroxyiminomalonate in which sodium nitrite and acetic acid are added to a mixture made from dimethyl malonate and water. The reaction mixture is extracted twice with dichloroethane, and the dimethyl hydroxyiminomalonate separated from the sodium acetate, which remains in the aqueous phase. Although the amounts of sodium nitrite used here are only 1.2 mol per mole of malonate, the reaction times of 21 hours make the reaction practically impossible to use for an industrial process. In addition, the process is not suitable for reacting malonic diesters of low water-solubility.

In all of the processes listed, the sodium acetate is produced as contaminated aqueous solutions which are difficult to dispose of. The processes are therefore unsuitable on environmental grounds for conversion to industrial scale.

DE 954 873 describes a process for preparing diethyl hydroxyiminomalonate, in which diethyl malonate is dissolved in a solvent which is not significantly water-miscible and which can be removed from the final product by distillation, for example toluene, and at least molar amounts of sodium nitrite, and also from 1 to 10% by weight of water, based on the malonic diester, are added to this solution, and glacial acetic acid is gradually added to the suspension at a temperature of from 30 to 70° C. until the nitrosation has been completed, and the reaction solution is separated off from undissolved sodium acetate, and diethyl hydroxyiminomalonate is crystallized from the solution. This process does not require solvent extraction and indeed about ⅔ of the sodium acetate is obtained as a solid. The process is said to give "smooth and rapid reactions and good yields". However, at least the latter is not the case, because the crystalline product obtained with a melting point of from 86.5 to 88° C. is certainly not the diethyl hydroxyiminomalonate, but its complex with sodium acetate. The product is so impure that the hydrogenation to give the diethyl acetaminomalonate on platinum catalysts in acetic anhydride, which is a particularly advantageous solvent, is impossible.

European Patent Application EP-A-0 811 607 describes a process with which C—H-acid compounds of the general formula II, and in particular those of low water-solubility, can be reacted with only a slight excess of alkali metal nitrite with a short reaction time and high conversion, and with good yields, to give hydroxyimino or nitroso compounds with the high purity required for downstream reactions. The salts produced here as byproducts can substantially be obtained in solid, reusable form, and the production of highly contaminated wastewater can be substantially or completely avoided.

The process of EP-A-0 811 607 consists in nitrosating compounds of the general formula II in the presence of water and of an inert organic solvent, using nitrous acid liberated from a nitrite by another acid. Use is made here of inert organic solvents or, respectively, solvent mixtures, in each case giving reaction mixtures which are as far as possible homogeneous. The most part of the salts derived from the reaction precipitate after the reaction, and can be removed by filtration.

Suitable solvents given in EP-A-0 811 607 are aliphatic or alicyclic ethers, such as dibutyl ether, methyl tert-butyl ether, tetrahydrofuran, 1,4-dioxane and dialkoxyalkanes. The examples of this European application mainly use 1,4-dioxane as solvent.

In the process described above there is >99% conversion of the compounds of the general formula II. Each of the nitrosation products is obtained in the form of the hydroxyimino compound or of the acetoxyimino compound, in yields of about 85% and with high purity.

EP A-0 811 607 expressly states that water is an indispensable constituent of the reaction mixture for the nitrosation reaction, since it permits and promotes the liberation of nitrous acid.

However, even if the process described in EPA-0 811 607 gives good yields of the corresponding nitrosation products, it nevertheless has numerous disadvantages.

The use of a solvent partially miscible with water, such as 1,4-dioxane, means that some or all of this solvent has to be removed from the reaction mixture after the reaction and prior to any further reaction, either by water-washing or by distillation. This is complicated and makes the preparation process considerably more expensive. In addition, the water-washing of the organic phase poses the problem that a not inconsiderable part of the abovementioned solvent passes into the washing water. The disposal of a resultant polluted wastewater is complicated and expensive. 1,4-Dioxane specifically, moreover, is a toxic solvent whose use is avoided where possible in industry.

EP-A-0 811 607 also describes the use of a second solvent, the addition of which after the nitrosation reaction brings about the substantial precipitation of the salts derived from the reaction. Methyl tert-butyl ether is highly suitable. To liberate the nitrous acid from the nitrite, the examples describe use acetic acid. After the nitrosation reaction and after the removal of the salts derived from the reaction, the reaction product is therefore present in a mixture of four different solvents—water, 1,4-dioxane, methyl tert-butyl ether and acetic acid. Prior to further reaction—usually catalytic hydrogenation of the hydroxyimino compound to the corresponding acetamido compound—at least some part of these solvents are removed by distillation. The resultant distillate requires complicated work-up or has to be discarded. In the abovementioned application, furthermore, the precipitation of the salts derived from the reaction has to be brought about by inoculation with sodium acetate trihydrate after the reaction. This is an exothermic process. An operation of this type is impossible and very difficult to carry out industrially, since it is impossible to insure sufficiently rapid dissipation of the heat of crystallization.

After the nitrosation of EP-A-0 811 607, a mixture of the corresponding hydroxyimino and acyloxyimino compounds is present. If the corresponding saturated acylamino compound is to be obtained from this by catalytic hydrogenation, the preliminary step of the reaction with excess carboxylic anhydride is needed, after purification and complete removal of the water. This insures that the only compound remaining is the acyloxy compound, which gives the saturated acylamino compound by hydrogenation. If, in contrast, a mixture of the hydroxyimino and acyloxyamino compounds is hydrogenated, the hydroxyimino compound can be consumed in a reaction to give the corresponding free amino compound. This compound is markedly more reactive than the corresponding acylamino compound and can cause considerable losses in yield, for example via polymerization.

SUMMARY OF THE INVENTION

One object of the present invention was therefore to provide a process which can convert C—H-acid compounds of the general formula II in a simple manner, by nitrosation followed by hydrogenation, and in high yields and with high purity, into the corresponding acylamino compounds. The number of solvents used here should be as small as possible, so that firstly the work-up of the reaction product and secondly the work-up of solvent mixtures produced can be made as simple as possible.

In addition, the salt produced in the reaction should precipitate as continuously as possible during the reaction, so that it is no longer necessary to add inoculation crystals for subsequent crystallization, and so that the uncontrolled generation of heat from the crystallization procedure can be avoided.

Acetimidomalonate intermediates are, moreover, more stable than oximes. Their stability is desirable for reasons both of safety and of yield optimization.

It has now been found that C—H-acid compounds of the general formula II can be converted in very good yields into the acyl compounds of the corresponding nitrosation products if the nitrosation is preferably carried out in an excess of the appropriate carboxylic anhydride.

Accordingly, the present invention provides a process for preparing amino derivatives of C—H acid compounds represented by formula I:

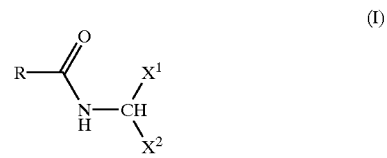

where
R is an unbranched or branched alkyl group having from 1 to 10 carbon atoms, in particular a methyl, ethyl or propyl radical, a cycloaliphatic radical having from 5 to 12 carbon atoms, an aryl radical, in particular the phenyl or the naphthyl radical, an alkylaryl radical having from 7 to 12 carbon atoms, such as the ethylphenyl radical, or an aralkyl radical having from 7 to 12 carbon atoms, such as the benzyl or the phenyl ethyl radical, and
$X^1$ and $X^2$ are identical or different electron-withdrawing groups, by reacting compounds represented by formula II:

where $X^1$ and $X^2$ are as defined above, with nitrous acid liberated from a nitrite by another acid, wherein the nitrosation is carried out in the presence of from 1 to 10 mol of a carboxylic anhydride (based on the compound of the formula II) thereby achieving complete conversion of the compound of the formula II, and the reaction product, the O-acyl derivative of the nitrosation product of II, is passed to a catalytic hydrogenation, optionally after removing the salts derived from the reaction.

The present invention also provides a process for preparing amino derivatives of C—H-acid compounds represented by formula I:

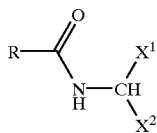

(I)

where
R is an unbranched or branched alkyl group having from 1 to 10 carbon atoms, a cycloaliphatic radical having from 5 to 12 carbon atoms, an aryl radical, an alkylaryl radical having a total of from 7 to 12 carbon atoms, or an aralkyl radical having a total of from 7 to 12 carbon atoms, and
$X^1$ and $X^2$ are identical or different electron-withdrawing groups, comprising:
reacting a C—H-acid compound represented by formula II:

(II)

where R, $X^1$, and $X^2$ are as defined above,
with nitrous acid liberated from a nitrite by an inorganic or organic acid, in the presence of from 1 to 10 equivalents of a carboxylic anhydride to produce an O-acyl derivative of the nitrosation product of the compound represented by formula II, and then
hydrogenating the O-acyl derivative of the nitrosation product of the C—H-acid compound represented by formula II.

In addition, the present invention also provides a process for preparing an O-acyl derivative of the nitrosation product of a C—H-acid compound represented by formula II:

(II)

where
$X^1$ and $X^2$ are identical or different electron-withdrawing groups, comprising:
reacting the C—H-acid compound represented by formula II with nitrous acid liberated from a nitrite by an inorganic or organic acid in the presence of from 1 to 10 equivalents of a carboxylic anhydride.

A more complete appreciation of the invention and many of the attendant advantages thereof will be readily obtained as the same becomes better understood by reference to the following detailed description.

DETAILED DESCRIPTION OF THE INVENTION

The C—H acid compound may advantageously form an initial charge together with the carboxylic anhydride and the suspended or dissolved nitrite, or it may be fed stepwise or continuously. The acid used to liberate the nitrous acid may be metered in at a prescribed temperature. The primary nitrosation product—the hydroxyimino compound—is immediately acylated under these reaction conditions and thus removed from the nitrosation equilibrium.

Surprisingly, the synthesis of the acyloxyimino compound of the corresponding C—H-acid compound of the general formula II succeeds with very high yields and short reaction times although there is almost no water in the reaction mixture. Traces of moisture which might pass into the reaction mixture via the C—H-acid compound or the alkali metal nitrite are very rapidly consumed by the carboxylic anhydride or by hydrate-forming salts. Thus, the reaction mixture is substantially free of water.

This finding is entirely surprising insofar as EP-A-0 811 607 maintains that water is an indispensable constituent of the reaction mixture for the nitrosation of C—H-acid compounds of the general formula II.

Although the abovementioned patent application states that small amounts of an acid anhydride may be used during the nitrosation reaction in order to scavenge water produced in the reaction, it explicitly states that these amounts of anhydride can be only small, in order that sufficient water is present in the mixture during the reaction. According to EPA-0 811 607, sufficient water content in the reaction mixture is a substantive precondition for a utilizable reaction rate.

In the process of the invention, the salt derived from the reaction precipitates continuously during the reaction, and inoculation after the nitrosation reaction can therefore be dispensed with. In addition, no hydroxyimino compound remains after the nitrosation reaction, but rather only the acyloxy compound, and therefore there is no longer any need for a preliminary reaction with an excess of anhydride after the nitrosation and removal of salts derived from the reaction and prior to the catalytic hydrogenation. The process of the invention therefore saves one step in the reaction.

After the reaction, the salt derived from the reaction can be removed by filtration, and the filtrate subjected to catalytic hydrogenation. This gives compounds of the general formula I in good yields and with high purities.

The electron-withdrawing groups $X^1$ and $X^2$ may be identical or different. $X^1$ and $X^2$ are preferably the groups —COOR', —C(NR')OR", —CONR'R", COR', where the definitions and preferred definitions of R' and R" are a hydrogen radical or preferably those given for R. $X^1$ and $X^2$ may also be a —CN or —$NO_2$ group.

Examples which may be mentioned of C—H-acid compounds particularly suitable as starting material for the process of the invention include:

malonic acid, and also its esters and imidoesters, such as dimethyl malonate, diethyl malonate, diisobutyl malonate, di-2-ethylhexyl malonate, dibenzyl malonate and diethyl monoimidomalonate; malonic amides or malonic amidoesters, such as malonamide, N,N'-dimethylmalonamide, N,N,N',N'-tetramethylmalonamide, and ethyl N,N-dimethylamidomalonate; malononitrile; cyanoacetic acid and its esters, such as ethyl cyanoacetate; β-keto acids and derivatives of these, such as acetoacetic acid and benzoylacetic acid, and esters and amides thereof, such as ethyl acetoacetate, N,N-dimethylacetoacetamide and ethyl benzoylacetate; 1,3-diketones, such as acetylacetone, benzoylacetone and dibenzoylacetone, and dibenzoylmethane; nitro compounds, such as dinitromethane, ethyl nitroacetate, and nitroacetonitrile; aromatic compounds with another electron withdrawing group flanking the —$CH_2$- group in general formula II, for example phenylacetic esters, phenylacetonitrile (benzyl cyanide), and 4-nitrophenylacetonitrile.

The ester groups in the abovementioned electron-withdrawing groups are unbranched or branched alkyl groups having from 1 to 12 carbon atoms, cycloaliphatic groups having from 5 to 12 carbon atoms, aryl groups, alkylaryl groups having a total of from 7 to 18 carbon atoms, or aralkyl groups likewise having from 7 to 18 carbon atoms. Alkyl groups in the other compounds mentioned contain in each case, independently of one another, from 1 to 10 carbon atoms. These ranges for the number of carbon atoms includes all specific values and subranges between the range endpoints listed above.

The actual nitrosating agent, the nitrous acid, is liberated in situ from a nitrite by another acid. Particularly suitable nitrites are alkali metal nitrites, such as sodium nitrite or potassium nitrite, and organic nitrites having unbranched or branched alkyl radicals which contain from 1 to 10 carbon atoms. The amounts used of these are generally from 1 to 3 mol per mole of C—H-acid compound II. The amount of nitrite advantageously used is from 1.0 to 1.7 mol, in particular from 1.05 to 1.4 mol, per mole of C—H-acid compound. These ranges for the number of carbon atoms includes all specific values and subranges therebetween, such as 1.02, 1.1, 1.15, 1.2, 1.25, 1.3, 1.35, 1.45, 1.5, 1.55, 1.6, and 1.7 mol.

Suitable acids which liberate the nitrous acid from the nitrite are any of the inorganic or organic acids which can protonate the nitrite at least to some extent. Suitable inorganic acids, inter alia, are hydrochloric acid, sulfuric acid, nitric acid and phosphoric acid. Among the suitable saturated or unsaturated organic acids, particular mention may be made of monocarboxylic acids having from 1 to 12 carbon atoms, for example formic acid, acetic acid and propionic acid, and of saturated or unsaturated dicarboxylic acids having from 2 to 14 carbon atoms, for example oxalic acid, malonic acid, glutaric acid, succinic acid, maleic acid and fumaric acid. The preferred inorganic acid is sulfuric acid and the preferred organic acid is acetic acid. The amount of the acid used is advantageously at least the stoichiometric amount corresponding to the nitrite. The acid to nitrite ratio is from 1:1 to 2:1, preferably from 1.0:1 to 1.8:1. However, particular preference is given to an approximately 1.6-fold stoichiometric excess. These ranges include all specific values and subranges therebetween, such as 1.1:1, 1.2:1, 1.3:1, 1.4:1, 1.5:1, 1.6:1, 1.7:1, and 1.9:1.

The carboxylic anhydrides used comprise mixed or symmetrical anhydrides, preferably acetic anhydride, propionic anhydride, butyric anhydride or benzoic anhydride. Clearly, one possibility is to select an anhydride which gives the desired acylamino compound, since the acyl derivatives derived from the corresponding hydroxyimino compounds and resulting from the nitrosation in the presence of the carboxylic anhydride are generally converted by subsequent catalytic hydrogenation into the corresponding acylamino compounds of the general formula I. Thus, the carboxylic anhydrides may be of the formula RC(=O)—O—C(=O)R.

The reaction may be carried out in the presence of from 1 to 10 equivalents of the carboxylic anhydride, based on the C—H-acid compound. It is preferable to use from 1.05 to 5 equivalents, very particularly preferably from 2 to 3 equivalents, of the carboxylic anhydride. ranges for the amount of carboxylic anhydride include all specific values and subranges therebetween, such as 1.1, 1.2, 1.5, 2, 2.5, 3, 3.5, 4, and 4.5 equivalents of the carboxylic anhydride.

The nitrosation by the process of the invention may be carried out at a pressure of from 0.8 to 20 bar, preferably at atmospheric pressure, and at a temperature of from 20 to 100° C., preferably at from 30 to 70° C., particularly preferably of from 40 to 60° C. These temperature ranges include all specific values and subranges therebetween, such as 25, 35, 45, 50, 75, 80, 90, and 95° C.

The reaction time needed for full conversion of the C—H-acid compound in the process of the invention, after completion of feeding of the other acid (metering time from about 1 to 4 hours, preferably from 2 to 3 hours), is from about 4 to 6 hours. The overall reaction time is therefore greater than that described in EP-A-0 811 607, but markedly less than that described in EP-A-0 517 041.

An additional advantage of the process of the invention is that downstream reaction with an anhydride is obviated, since the corresponding acetoxyimino compound is the direct reaction product from the nitrosation. The reaction time for this additional stage is therefore saved.

In the process of the invention the work-up or further processing of the reaction product by catalytic hydrogenation is very simple.

In the event that inorganic nitrites are used, the salts derived from the reaction may first be removed by filtration or centrifuging. After a further precipitation using an inert organic solvent, such as methyl tert-butyl ether (MTBE) or toluene and then filtering again or centrifuging again, where appropriate, the filtrate is catalytically hydrogenated under the usual conditions. This gives the corresponding acylamino compound of the general formula I in an overall yield of from 85 to 95%. This range includes all specific values and subranges therebetween, such as 88, 90, and 92%.

However, after the main part of the salts derived from the reaction have been removed by filtration or centrifuging, it is also possible for some part of the low-boilers, such as acetic acid and acetic anhydride, first to be distilled off, where appropriate in vacuo, and for the residue to be taken up in an inert organic solvent, such as methyl tert-butyl ether, and the organic phase washed with water in order to remove residues of salt.

The catalytic hydrogenation (i.e., hydrogenating in the presence of a in the presence of a hydrogenation catalyst) can then be accomplished using procedures well-known to those skilled in the art. Procedures for the catalytic hydrogenation are described in, for example, W. Carruthers, "Some Modem Methods of Organic Synthesis," Third Edition, Cambridge University Press, 1986, pages 411–431, incorporated herein by reference.

As is well-known to those skilled in the art, compounds of the general formula I are useful intermediates for compounds which can be used in the pharmaceutical and agricultural sectors.

EXAMPLES

Having generally described this invention, a further understanding can be obtained by reference to certain specific examples which are provided herein for purposes of illustration only and are not intended to be limiting unless otherwise specified.

Example 1

0.67 mol of acetic acid is fed into a mixture made from 0.38 mol of diethyl malonate, 1.14 mol of acetic anhydride and 0.5 mol of sodium nitrite, with stirring, at a temperature of 40° C., in such a way as to prevent the reaction temperature from exceeding 50° C. (metering time: about 3 hours). Stirring is continued for 4 hours at 50° C., followed by cooling to room temperature. Salts derived from the reaction are filtered off, and the salt is then washed with about 100 ml of methyl tert-butyl ether. The sodium acetate from the post precipitation is filtered off, and the mother liquor is mixed with 5 g of platinum/carbon (5%). The mixture is hydrogenated at a hydrogen pressure of 5 bar and a temperature of from 45 to 50° C.Hydrogen uptake ceases after about 4 hours. The mixture is cooled and the pressure released, and some of the solvent is removed by distillation in vacuo. After crystallization of the product the solid is isolated by filtration. This gives a yield of 85% of diethyl acetylaminomalonate.

Example 2

The same procedure as Example 1 was used except
Metering time: 3 hours
After-reaction: 1 hour at 40° C.
3 hours at 30° C.
Filtration, removal of low-boilers by distillation
Take-up in MTBE, washing with water,
hydrogenation under the above conditions
Yield: 90%

Example 3

2.28 mol of diethyl malonate
6.84 mol of acetic anhydride
3.78 mol of sodium nitrite
6.0 mol of acetic acid
are introduced as an initial charge at 40° C., dropwise addition to take place within a period of 3 hours, continued stirring for 4 hours at 50° C., filtration, hydrogenation as above.
Yield: 87%

Example 4

2.28 mol of diethyl malonate
6.84 mol of acetic anhydride
3.78 mol of amyl nitrite
6.0 mol of acetic acid
The experiment was carried out as in Experiment 3.
1 Yield: 78%

Example 5

2.28 mol of dibenzyl malonate
6.84 mol of acetic anhydride
3.78 mol of sodium nitrite
6.0 mol of acetic acid are introduced as an initial charge at 40° C., dropwise addition to take place within a period of 3 hours, continued stirring for 4 hours at 50° C., filtration, hydrogenation as above.
Yield: 82%

Obviously, numerous modifications and variations of the present invention are possible in light of the above teachings. It is therefore to be understood that within the scope of the appended claims, the invention may be practiced otherwise than as specifically described herein.

This application is based on German patent application serial No. 10026108.5, filed on May 26, 2000, the contents of which are incorporated herein by reference.

What is claimed is:

1. A process for preparing an amino derivative of a C—H-acid compound represented by formula I:

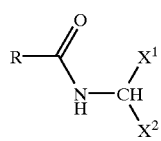

wherein
R is an unbranched or branched alkyl group having from 1 to 10 carbon atoms, a cycloaliphatic radical having from 5 to 12 carbon atoms, an aryl radical, an alkylaryl radical having a total of from 7 to 12 carbon atoms, or an aralkyl radical having a total of from 7 to 12 carbon atoms, and $X^1$ and $X^2$ are identical or different electron-withdrawing groups, comprising:

reacting a C—H-acid compound represented by formula II:

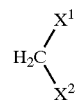

wherein R, $X^1$, and $X^2$ are as defined above, with nitrous acid liberated from a nitrite by an inorganic or organic acid, in the presence of from 1 to 10 equivalents of a carboxylic anhydride to produce an O-acyl derivative of the nitrosation product of the C—H-acid compound represented by formula II, and then hydrogenating the O-acyl derivative of the nitrosation product of the C—H-acid compound represented by formula II in the presence of a hydrogenation catalyst, wherein the reaction mixture is substantially free of water.

2. The process of claim 1, wherein the salt derived from the reaction is removed prior to the hydrogenation of the O-acyl derivative of the nitrosation product of the C—H-acid compound represented by formula II.

3. The process of claim 1, wherein the electron-withdrawing groups $X^1$ and $X^2$ are independently selected from the group consisting of —COOR', —C(NR')OR", —CONR'R", COR', —CN, and —NO$_2$, wherein R' and R" are, independently, a hydrogen radical, an unbranched or branched alkyl group having from 1 to 10 carbon atoms, a cycloaliphatic radical having from 5 to 12 carbon atoms, a phenyl radical, a naphthyl radical, an alkylaryl radical having from 7 to 12 carbon atoms, or an aralkyl radical having from 7 to 12 carbon atoms.

4. The process of claim 1, wherein the C—H-acid compound is selected from the group consisting of malonic acid, esters of malonic acid, imidoesters of malonic acid, malonamides, malonamidoesters, malononitrile, cyanoacetic acid, esters of cyanoacetic acid, β-keto acids, derivatives of β-keto acids, 1,3-diketones, nitro compounds, and aromatic compounds having another electron-withdrawing group flanking the —CH$_2$-group in formula II.

5. The process of claim 4, wherein the C—H-acid compound is selected from the group consisting of dimethyl malonate, diethyl malonate, diisobutyl malonate, di-2-ethylhexyl malonate, dibenzyl malonate, diethyl monoimidomalonate, malonamide, N,N'-dimethylmalonamide, N,N,N',N',-tetramethylmalonamide, ethyl N,N-dimethylamido malonate, malononitrile, ethyl cyanoacetate, acetoacetic acid, benzoylacetic acid, ethyl acetoacetate, N,N-dimethylacetamide, ethyl benzoylacetate, acetylacetone, benzoylacetone, dibenzoylacetone, dibenzoylmethane, dinitromethane, ethyl nitroacetate, nitroacetonitrile, phenylacetic esters, phenylacetonitrile (benzyl cyanide), and 4-nitrophenylacetonitrile.

6. The process of claim 1, wherein the nitrite is an alkali metal nitrite.

7. The process of claim 1, wherein the amount of the nitrite is from 1 to 3 mol per mole of the C—H-acid compound.

8. The process of claim 1, wherein the inorganic acid is selected from the group consisting of sulfuric acid, nitric acid, and phosphoric acid, in a ratio of from 1 to 2 mol of the inorganic acid to 1 mol of the nitrite.

9. The process of claim 1, wherein the organic acid is selected from the group consisting of formic acid, acetic acid, and propionic acid, in a ratio of from 1 to 2 mol of the organic acid to 1 mol of the nitrite.

10. The process of claim 1, wherein the carboxylic anhydride is selected from the group consisting of acetic anhydride, propionic anhydride, butyric anhydride, and benzoic anhydride.

11. The process of claim 1, wherein the nitrosation is carried out at a pressure of from 0.8 to 20 bar and at a temperature of from 20 to 100° C.

12. The process of claim 1, wherein the salts derived from the reaction are removed by filtration or centrifuging, and the filtrate is catalytically hydrogenated.

13. The process of claim 1, wherein the aryl radical is a phenyl radical or a naphthyl radical.

14. The process of claim 1, wherein $X^1$ and $X^2$ are, independently, selected from the group consisting of —COOR', —CN, and —NO$_2$.

15. The process of claim 1, wherein R is an unbranched or branched alkyl group having from 1 to 10 carbon atoms, a phenyl radical, or a benzyl radical.

16. The process of claim 1, wherein the electron-withdrawing groups $X^1$ and $X^2$ are independently selected from the group consisting of —COOR', —C(NR')OR'', —CONR'R'', COR', and —NO$_2$, wherein
R' and R'' are, independently, a hydrogen radical, an unbranched or branched alkyl group having from 1 to 10 carbon atoms, a cycloaliphatic radical having from 5 to 12 carbon atoms, a phenyl radical, a naphthyl radical, an alkylaryl radical having from 7 to 12 carbon atoms, or an aralkyl radical having from 7 to 12 carbon atoms;
nitrite is an alkali metal nitrite;
the inorganic acid is selected from the group consisting of sulfuric acid, nitric acid, and phosphoric acid;
the organic acid is selected from the group consisting of formic acid, acetic acid, and propionic acid;
the carboxylic anhydride is selected from the group consisting of acetic anhydride, propionihydride, butyric anhydride, and benzoic anhydride.

17. The process of claim 16, wherein R is an unbranched or branched alkyl group having from 1 to 10 carbon atoms, a phenyl radical, or a benzyl radical.

18. The process of claim 1, wherein the hydrogenation catalyst comprises platinum.

19. A process for preparing an amino derivative of a C—H-acid compound represented by formula I:

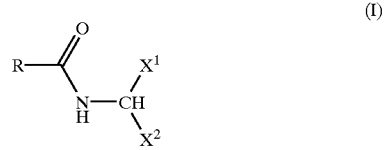

wherein
R is an unbranched or branched alkyl group having from 1 to 10 carbon atoms, a cycloaliphatic radical having from 5 to 12 carbon atoms, an aryl radical, an alkylaryl radical having a total of from 7 to 12 carbon atoms, or an aralkyl radical having a total of from 7 to 12 carbon atoms, and
$X^1$ and $X^2$ are identical or different electron-withdrawing groups, comprising:
reacting a C—H-acid compound represented by formula II:

wherein R, $X^1$, and $X^2$ are as defined above, with nitrous acid liberated from a nitrite by an inorganic or organic acid, in the presence of from 1 to 10 equivalents of a carboxylic anhydride to produce an O-acyl derivative of the nitrosation product of the compound represented by formula II, and then
hydrogenating the O-acyl derivative of the nitrosation product of the C—H-acid compound represented by formula II, wherein the reaction mixture is substantially free of water.

20. A process for preparing an O-acyl derivative of the nitrosation product of a C—H-acid compound represented by formula II:

wherein
$X^1$ and $X^2$ are identical or different electron-withdrawing groups, comprising:
reacting the C—H-acid compound represented by formula II with nitrous acid liberated from a nitrite by an inorganic or organic acid in the presence of from 1 to 10 equivalents of a carboxylic anhydride, wherein the reaction mixture is substantially free of water.

* * * * *